(12) United States Patent
Faccioli et al.

(10) Patent No.: US 9,408,697 B2
(45) Date of Patent: Aug. 9, 2016

(54) BIOMATERIAL AND METHOD FOR ITS REALISATION

(75) Inventors: Giovanni Faccioli, Monzambano (IT); Renzo Soffiatti, Nogara (IT)

(73) Assignee: TECRES S.P.A., Verona (IT)

( * ) Notice: Subject to any disclaimer, the term of this patent is extended or adjusted under 35 U.S.C. 154(b) by 130 days.

(21) Appl. No.: 13/994,612

(22) PCT Filed: Dec. 14, 2010

(86) PCT No.: PCT/IB2010/055815
§ 371 (c)(1), (2), (4) Date: Jun. 14, 2013

(87) PCT Pub. No.: WO2012/080782
PCT Pub. Date: Jun. 21, 2012

(65) Prior Publication Data
US 2013/0274891 A1 Oct. 17, 2013

(51) Int. Cl.
*A61F 2/28* (2006.01)
*A61K 9/00* (2006.01)
*A61L 27/56* (2006.01)
*A61L 31/12* (2006.01)
*A61K 35/32* (2015.01)
*A61L 24/00* (2006.01)
*A61L 24/06* (2006.01)
*A61L 27/16* (2006.01)
*A61L 27/46* (2006.01)

(52) U.S. Cl.
CPC ............... *A61F 2/28* (2013.01); *A61K 9/0024* (2013.01); *A61K 35/32* (2013.01); *A61L 24/0036* (2013.01); *A61L 24/0084* (2013.01); *A61L 24/06* (2013.01); *A61L 27/16* (2013.01); *A61L 27/46* (2013.01); *A61L 27/56* (2013.01); *A61L 2400/16* (2013.01); *A61L 2430/02* (2013.01)

(58) Field of Classification Search
CPC . A61K 2300/00; A61K 35/32; A61K 9/0024; A61L 27/56; A61L 2430/02
See application file for complete search history.

(56) References Cited

U.S. PATENT DOCUMENTS

| 5,085,861 A | 2/1992 | Gerhart et al. |
| 2005/0074415 A1* | 4/2005 | Chow .................. A61K 6/0038 424/49 |
| 2007/0059281 A1 | 3/2007 | Moseley et al. |
| 2007/0191963 A1* | 8/2007 | Winterbottom et al. ..... 623/23.5 |

FOREIGN PATENT DOCUMENTS

| EP | 1891984 | 2/2008 |
| WO | WO02056928 | 7/2002 |
| WO | WO2008037991 | 4/2008 |

* cited by examiner

*Primary Examiner* — Frederick Krass
*Assistant Examiner* — Tracy Liu
(74) *Attorney, Agent, or Firm* — Tutunjian & Bitetto, P.C.

(57) ABSTRACT

Porous biocompatible composite biomaterial, useable as a drug delivery system or as spacer or as bone substitute, such as for example for filling bone lacunae or for substituting damaged parts of bone tissue, or for fixing prosthesis of various types, or for thickening bones weakened by illness such as osteoporosis or the like, including a component adapted to form a porous structural matrix and a soluble component, wherein the soluble component is in form of powder and granules or other similar agglomerates so as to have mechanical support characteristics and osteoinductive and osteoconductive characteristics in the entire volume occupied by the biomaterial, and a method for obtaining the biomaterial.

20 Claims, 2 Drawing Sheets

BIOMATERIAL AND METHOD FOR ITS REALISATION

TECHNICAL FIELD OF THE INVENTION

The present invention regards a biomaterial useable in the medical field, having high characteristics of integration with the biological system in which it is interfaced, bioinductivity and bioconductivity characteristics.

The present invention further regards a method for obtaining a biomaterial having high characteristics of integration with the biological system in which it is interfaced, bioinductivity and of bioconductivity characteristics.

DESCRIPTION OF RELATED ART

Ceramic and/or polymeric biomaterials substantially used for fixing prosthesis or as bone substitutes are currently the most commonly used in the field of biomaterials, in particular biomaterials useable in the orthopaedic and surgery field, for filling cavities or lacunae of various origin and type.

Such polymeric biomaterial includes, for example, acrylic bone cement, possibly made up of polymethylmethacrylate (PMMA) and methylmethacrylate (MMA), and absorbable cements, the latter used in cases where the support function that they are required to perform is limited over time.

Ceramic biomaterials are, usually, polycrystalline aggregates constituted by an ordered series of elements joined together by strong bonds. Such ceramic biomaterials can be bioactive, i.e., induce—in the biological tissues—a response upon the occurrence of chemical and physical processes on the biomaterial/biological tissue interface.

Active ceramic biomaterials include, for example, calcium phosphate salts (CPC), among which the most commonly used are hydroxyapatite (HA), alpha-tricalcium phosphate ($\alpha$-TCP) and beta-tricalcium phosphate ($\beta$-TCP), which have a high biocompatibility and an ideal bioconductivity.

However such materials reveal some drawbacks.

Acrylic cement has optimal mechanical performance which guarantees functional implants even lasting twenty years. However, it does not develop a chemical bond with the bone tissue and the mechanical resistance thereof is essentially based on the friction on the interface with the prosthesis and the bone; furthermore, it cannot be absorbed.

Though biocompatible and at least partly absorbable, calcium phosphate cements instead, reveal poor mechanical resistance.

A method for producing a biocompatible polymeric/ceramic composite material with a predetermined porosity, designed and determined previously, is also known.

Such method comprises a first step of preparing a suspension of a ceramic biomaterial in water, a second step in which a compact of ceramic biomaterial containing the desired amount of water is obtained from this suspension and a third step of mixing such compact with a polymeric material and/or with a liquid monomer.

The composite material obtained from the method described in the abovementioned patent application, as well as other biomaterials based on polymeric matrix and particles which can be dissolved in a stage subsequent to the preparation one, for example calcium phosphate, combine the characteristics of biocompatibility and absorbability, for example of calcium phosphate, with the mechanical resistance of polymeric cement.

However, the methods for obtaining such materials are extremely complex and difficult and they have not lead to any commercial product up to date; furthermore, though potentially osteoinductive and osteoconductive, the polymeric/ceramic materials allow bone colonization solely in the most external and surface area thereof and they are not capable of obtaining a complete in-depth colonization of the bone.

It is known that a biomaterial of suitable porosity, when arranged in a vital bone tissue, is invaded by such tissue only if the cavities have—in the biomaterial—a dimension larger than 100 microns.

On the contrary, when a non-porous biomaterial is arranged in a bone tissue, a fibrous tissue cover, referred to as fibrous sheath, is generated at the interface between the biomaterial and the bone tissue.

The formation of such fibrous sheath insulates the biomaterial from the bone, prevents integration and regeneration thereof and it is thus harmful, also due to the fact that in such a manner such sheath constitutes an interruption or discontinuity between the cement and the bone and hinders the possibility of bearing high mechanical loads.

In an attempt to counter the occurrence of such fibrous sheath, the most standard procedure is that of using biomaterials which have surface cavities adapted to receive the newformation of the bone tissue. The newly-formed bone is implanted into such porosity thus improving the adhesion between the biomaterial and the bone tissue.

The solutions used currently and described above, however, did not obtain the expected tissue regeneration and implantation, as visible in FIG. 1, due to the fact that the spread porosity does not have cavities larger than 100 microns.

For example, some materials, such as ceramic materials, due to a largely spread porosity, conferred by large intercommunicating cavities with dimension comprised between 200 and 500 microns, are capable of obtaining the tissue regeneration inside the material but to the detriment of mechanical resistance. Thus, the use of such biomaterials is limited to a bone filler not subjected to direct loads. Actually, such materials are used as cranial prosthesis, which however, if subjected to impacts or loads, can break without guaranteeing suitable resistance characteristics required even in such part of the human body.

The previously described biomaterials do not meet all the requirements suitable for supporting and possibly quickening such tissue growth.

Thus, there arises the need of providing a biomaterial which, alongside having good mechanical resistance, is capable of allowing the regeneration of the tissue with which it is to be interfaced, for use in the orthopaedic field, dental field etc. Such tissue is in particular the bone tissue.

Actually, tissue regeneration requires a suitable support, conferred by the biomaterial, which, as previously indicated, requires having conductive and inductive characteristics with respect to the tissue to be regenerated.

SUMMARY OF THE INVENTION

Thus, the object of the present invention is that of improving the prior art.

Within such technical task, the present invention aims at providing a biomaterial adapted to be interfaced with organic tissues without creating adverse reactions in the tissue or at systemic level.

Another object of the present invention is that of providing a biomaterial having bioinductive and bioconductive characteristics, in particular osteoinductive and osteoconductive. A further object of the present invention is that of providing a biomaterial adapted to allow the colonization—therein—of the organic tissue with which it comes into contact, simultaneously guaranteeing good mechanical resistance characteristics.

These and other objects are all attained by the biomaterial according to one or more of the attached claims.

Within such technical field, providing a method for obtaining a biomaterial adapted to be interfaced with organic tissues without creating adverse reactions in the tissue or at systemic level constitutes an object of the present invention.

Another object of the present invention is that of providing a method for obtaining a biomaterial having bioinductive and bioconductive characteristics, in particular osteoinductive and osteoconductive.

Another object of the present invention is that of providing a method for obtaining a biomaterial adapted for allowing colonization—therein—of the organic tissue with which it comes into contact, simultaneously guaranteeing good mechanical resistance characteristics. Another object of the present invention is that of providing a method that can be easily obtained by clinicians and technicians using the materials currently available in the market.

Still another object of the present invention is that of providing a method that is inexpensive.

These and other objects are attained by the method for obtaining a biomaterial according to one or more of the attached claims.

An important advantage attained by the biomaterial according to the present invention is that of having the possibility of being present in at least two versions: in solid form, possibly preformed and resizable through the common orthopaedic equipments according to the prior art, or in form of a pasty fluid, which can possibly be injected or applied onto the prearranged seat through known syringe, blade means or the like.

A further advantage lies in the possibility of applying the biomaterial according to the present invention through the techniques of the prior art and universally known by clinician, trained for use thereof, thus without requiring retraining the personnel intended to use and apply such biomaterial.

Another advantage lies in the possibility of obtaining the biomaterial according to the following invention starting from commonly used materials and using instruments and accessories commonly available for those skilled in the art.

A further advantage attained by the method for obtaining a biomaterial according to the present invention is that of being applicable to materials available and known by a man skilled in the art.

A further advantage of the method for obtaining a biomaterial according to the present invention is that of having the possibility of conferring the properties required to obtain tissue regeneration even using low cost materials, usually rarely used in the sector.

BRIEF DESCRIPTION OF THE DRAWINGS

These and other advantages shall be clearer to those skilled in the art from the following description and from the attached drawings, provided by way of non-limiting example, wherein.

DETAILED DESCRIPTION

Figure 1:
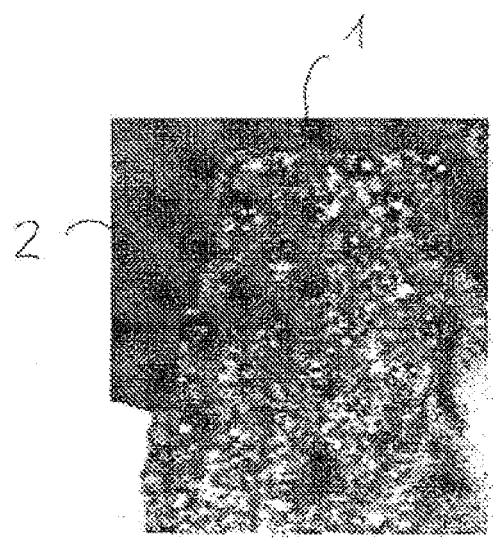
FIG. 1 illustrates a section of a bone tissue and prior art polymeric-ceramic biomaterial in which there is the growth of a newly formed bone tissue solely in the outer porous part.

In the present disclosure, the term biomaterial is used to indicate material of any type or origin capable of interfacing with a biological system with the aim of increasing, treating or substituting any organ tissue or body function; the term bioinductivity is used to indicate the capacity of the biomaterial to cause the new-formation of the tissue with which such biomaterial is interfaced; the term bioconductivity is used to indicate the capacity of the biomaterial to create a suitable support, adapted to allow the colonisation of the progenitor cells of the tissue with which such material is interfaced and capable of guaranteeing survival and proliferation thereof.

The biomaterial according to the present invention is a biocompatible composite material comprising a component adapted to form a porous structural matrix.

Such component adapted to form a porous structural matrix may comprise polymeric components, pure metal components or made of alloy and/or ceramic components, as long as they are biocompatible.

The component adapted to form a porous structural matrix which constitutes the biomaterial according to the present invention determines the structural support of the biomaterial and confers good mechanical characteristics thereto, greater than those of the ceramic materials and comparable to those of classic acrylic cements, such to allow even the application of direct loads like in the case in which a vertebral body is filled with such biomaterial, for example in the known surgical technique called vertebroplasty. Such biomaterial is thus not fragile.

The biomaterial according to the present invention further comprises a soluble component.

Such soluble component can be made up of calcium bioceramic inorganic material such as for example tricalcium phosphate (TCP), calcium sulphate (CS) and calcium carbonate (CC).

Such soluble component can also be made up of other inorganic salts provided with solubility and biocompatibility such as sodium chloride, potassium chloride or magnesium and aluminum salts. Soluble organic substances for example polysaccharides such as lactose and carbohydrates such as amides can also be used. Such soluble component is in form of powder and granules or other similar agglomerates.

The soluble component in form of powder has a dimension substantially smaller than 100 microns while the soluble component in form of granules or other similar agglomerates has a dimension substantially larger than 100 microns and preferably comprised between 200 and 500 microns.

The soluble component which forms the biomaterial according to the present invention has the capacity, upon contact with water and/or liquids of various types and/or biological liquids, of dissolving and/or solubilizing; it is thus eliminated from the biomaterial, leaving the corresponding empty spaces to form a porosity in form of open microcavities and macrocavities, interconnected to each other, which make all the cavities present in the biomaterial intercommunicating.

The microcavities, originating from the dissolution of the soluble component in form of powder, are summed with the "canaliculi," already present in the structural matrix, also with dimension smaller than 100 microns which converge or are connected or joined, alongside the microcavities, with the macrocavities.

The microcavities and canaliculi, due to the small dimension thereof, minimize the mechanical deterioration of the biomaterial and allow the capillary invasion by the biological fluids present in the surrounding bone tissue and the corresponding migration of growth factors or of osteogenic factors, required for promoting bone growth. Such factors reach up to the macrocavities, which, originated from the soluble component in form of granules or other similar agglomerates, have a dimension larger than 100 microns.

The macrocavities may be substantially spherical-shaped. Such macrocavities preferably have a dimension comprised between 200 and 500 microns.

The macrocavities and microcavities are obtained from the soluble component and substantially they have the shape of such soluble component.

Due to the porous nature thereof and the capacity of absorbing liquids through capillarity, the biomaterial according to the present invention can be advantageously used as a drug delivery system with the aim of containing and administering active ingredients even serving as drugs in the place of arrangement.

The soluble component is homogeneously distributed within the biomaterial; analogously the porosity in form of micro and macrocavities is present homogeneously over the entire mass of the biomaterial.

The biomaterial according to the present invention may possibly comprise a moisture level variable in percentage, possibly in form of water or aqueous solutions. Such humidity is used to determine the formation of the previously described "canaliculi," in the structural matrix. The "canaliculi" can house, partly, the soluble component.

The biomaterial according to the invention can be arranged in a bone lacuna or seat with the aim of filling it so as to restore the structural continuity thereof. Such structural continuity is attained due to the proliferation of a new bone tissue within the biomaterial.

Actually, the biomaterial according to the present invention allows uninterruptedly joining a synthetic material, like the biomaterial, and a biological tissue. Actually, such biomaterial "merges" with the bone tissue becoming a continuous and non-separable part thereof, eliminating the discontinuity typical of similar products.

Experimental tests carried out by the Applicant revealed that the bone growth within a solid biomaterial can be promoted or prevented depending on the need.

In particular, in order to promote bone regeneration, the biomaterial should meet at least three conditions: 1) the biomaterial should be covered with open microcavities, interconnected to each other, which make all the cavities present in the biomaterial intercommunicating; the average dimensions of said microcavities, usually smaller than 100 microns, should be sufficiently small to allow filling with liquid through capillary force; 2) the biomaterial should also contain macrocavities with dimension larger than 100 microns and substantially spherical-shaped; 3) the biomaterial should be surrounded by living bone tissue.

On the contrary, failure to meet just one of the previously outlined requirements is enough to prevent bone growth within a porous biomaterial.

The biomaterial according to the present invention meets such requirements: actually, it has the right-sized porosity which, besides facilitating and causing bone regeneration therein, is capable of absorbing—through capillarity—fluids of various types, gaseous substances and/or water or other biological liquids and/or drugs and medicinal substances. Such biomaterial is then capable of delivering such substances again outside and making them available therein.

Furthermore, the fact that the soluble component in granules or other similar agglomerates, and the ensuing macrocavities, is alternated with a soluble component in powder form, with ensuing microcavities, allows meeting the required mechanical characteristics of the biomaterial which can thus be subjected to direct loads.

In the currently known materials, the macrocavities are solely present in the peripheral zone of the material. The inner part instead contains microcavities alone. This determines a tissue infiltration 1 of the bone 2 only at the peripheral part of the material used which, therein, is not colonized by a new tissue, as observable in FIG. 1.

Figure 2:
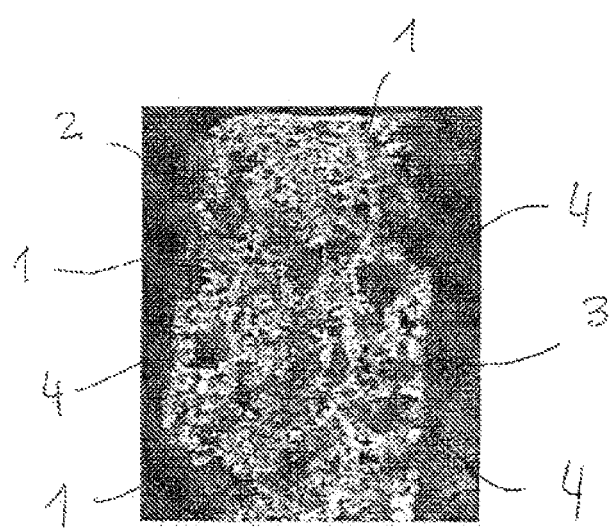
FIG. 2 illustrates a section of a bone tissue and biomaterial according to the present invention in which there is the growth of the newly formed bone tissue in the entire free volume of the biomaterial.

The biomaterial 3 according to the present invention, due to the abovementioned homogeneous distribution of the soluble component in form of powder and granules or similar agglomerates, instead, determines the presence of macrocavities 4, correlated to each other and with the microcavities, both in the surface and inner part of the biomaterial. Thus, the colonization of the newly formed bone 1 occurs on all the free zones of the biomaterial, up to the complete integration of the bone 2 up to the centermost part of the biomaterial, as observable in FIG. 2.

Figure 3:
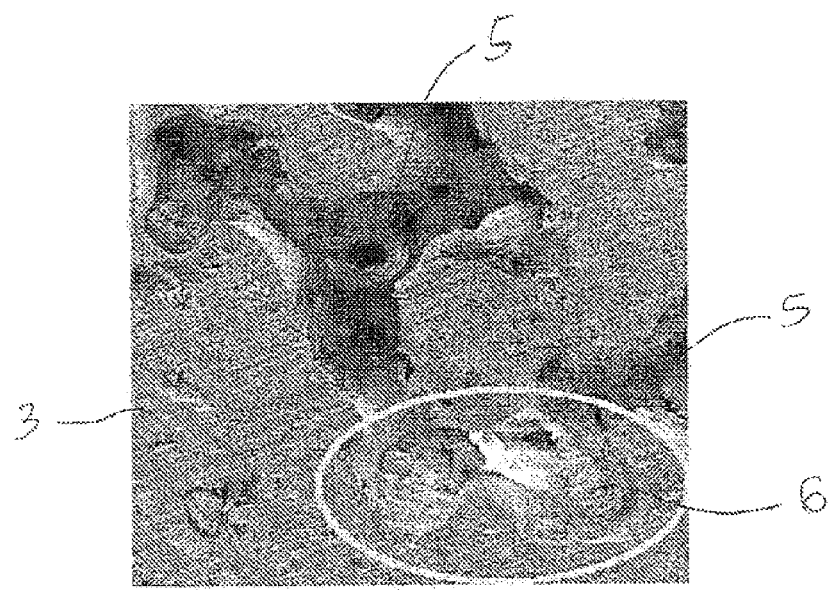
FIG. 3 illustrates an enlarged detail of the biomaterial according to the present invention.

FIG. 3 shows an enlargement of the biomaterial 3 in which the "canaliculi" 5, inside which there is a part of the soluble component 6, are observed.

Scientific tests show that the cells of the bone tissue colonizing the biomaterial according to the present invention, initially progenitor cells of the bone tissue or osteoblasts, are transformed into osteocytes over time, i.e., an actual solid and mineralized bone tissue. Thus, the bone tissue grows and matures within the biomaterial, thus allowing the correct growth and nutrition of the cells by which it is colonized in-depth.

Furthermore, contrary to the previous belief, it was proved that the bone tissue grows even in terms of cavities with dimension smaller than 100 microns, in case there are more inner macrocavities which cause proliferation thereof.

Thus, the biomaterial according to the present invention is a biocompatible biomaterial, having osteoinductive and osteoconductive characteristics which allow the bone regeneration of the entire free volume occupied by the biomaterial. Thus the macrocavities serve as "recall" for the osteoid bone tissue, which reaches them, migrating through the microcavities. Also the microcavities are filled with the newly formed osteoid tissue but solely in case of presence of macrocavities: if such macrocavities are absent, the osteoid tissue does not enter the microcavities. The presence of microcavities alongside intercommunicating macrocavities is thus an essential requirement to obtain the biomaterial according to the present invention having osteoinductive and osteoconductive characteristics.

Furthermore, the presence of such type of micro and macrocavities confers the previously mentioned bioactivity characteristics also to a previously inert material.

Such biomaterial can be used, for human beings and/or animals, for insertion in fractured bones or that have been weakened following a disease such as osteoporosis, or for positioning in bone lacunae generated by partial therapeutic surgical removal of bone tissue (for example due to a tumour), with the aim of reinforcing them, preventing or reducing further weakening of the tissue. Actually, the biomaterial according to the present invention stimulates osteogenesis so that the new bone is produced in the nearby areas. Such new-formation continues up to the complete invasion of the biomaterial. Thus, such biomaterial remains firmly anchored to the pre-existent bone, thus becoming a structural part thereof capable of bearing mechanical stresses involving the organ. In a further embodiment, the previously described biomaterial can be added with radiopaque materials, for example barium sulphate and/or other known radiopaque materials.

The biomaterial according to the present invention has the double possibility of being available in preformed solid form or fluid paste which can be injected through standard means currently used for the known materials.

The fact that the biomaterial can be present in these two forms is conferred by the capacity of the component adapted to constitute a porous structural matrix to be in fluid or previously solidified form.

The component adapted to form a structural matrix in fluid form has the capacity of solidifying within a predetermined period of time.

In the form of fluid paste, such biomaterial can thus be inserted into an extrusion syringe or similar extrusion means and for example, positioned in a vertebra through percutaneous means.

In the preformed solid form, which can for example be derived from a previously solidified fluid form or from sintering the same, for example in form of a 20×20×20 mm parallelepiped, or blocks of any other size or shape, the biomaterial can be easily resized through common orthopaedic equipment. The obtained fragment can be usefully arranged in a bone lacuna. The biomaterial will be colonized by the newly formed bone tissue within a short period of time.

Thus, the biomaterial according to the present invention acquires several therapeutic applications.

Table 1 describes an embodiment of the biomaterial according to the present invention and describes the mechanical characteristics of various materials compared.

TABLE 1

| Material | Glass transition temperature Tg (° C.) | Resistance to flexion (MPa) | Elasticity modulus (MPa) | Resistance to traction (MPa) | Resistance to compression (MPa) |
|---|---|---|---|---|---|
| Cortical bone | — | 49-148 | 11-19 | — | 131-205 |
| Spongious bone | — | — | 9-32 | — | 2 |
| Porous ceramic | — | 1-2 | 8 | — | 10-15 |
| Porous PMMA withTCP granules | 110 | 17 | 1.17 | — | 36 |
| PMMA | 110 | 70 | 3 | 50 | 100 |
| 316steel | — | 280 | 200 | 515 | — |

The method for obtaining the biocompatible composite material according to the present invention, useable as bone substitute, such as for example for filling bone lacunae or for substituting damaged parts of bone tissue, or for fixing prosthesis of various types, or for thickening bones weakened by illness such as osteoporosis or the like, comprises the steps of obtaining a component adapted to form a porous structural matrix and provision of a soluble component in form of powder and granules or other similar agglomerates.

This step of obtaining the component adapted to form a porous structural matrix is attained by providing one or more components selected from the group comprising: polymeric components, and/or pure metal components and/or in alloys, and/or ceramic components.

The abovementioned step of obtaining the soluble component is attained by providing a material in form of powder with dimension smaller than 100 microns and in form of granules or other similar agglomerates with dimension larger than 100 microns and preferably with dimension comprised between 200 and 500 microns.

The method according to the present invention comprising a step of mixing the component adapted to form a porous structural matrix and the soluble component.

The method according to the present invention comprising a step of thermal polymerisation or solidification or thermal sintering of the biomaterial.

In an embodiment, the step of obtaining the component adapted to form a preformed structural matrix is attained by providing a polymeric and/or metal and/or ceramic component and a step for thermal sintering the same.

In an example, such embodiment provides for the provision of the component adapted to form a structural matrix, in form of polymer, and/or ceramic, and/or metal, in powder form having suitable grain size, the addition of said component adapted to form a structural matrix with a soluble component in form of soluble salts, such as soluble ceramics in form of powder and granules, and, possibly, with accessory substances serving as expanding agents, for example an expanding material.

Such method further comprises the steps of transferring the entire assembly into a heating chamber; closing and pressurizing the heating chamber; melting, due to the high temperature and to the high pressure, at least at the interface, the particles of material of said component adapted to form a structural matrix, expanding the expanding material, producing a weft/mesh of thin intercommunicating canaliculi in the component adapted to form a structural matrix.

Such method further comprises a step of entrapping the single particles of soluble ceramic in powder and granular form in the component adapted to form a structural matrix, and interconnection thereof by the weft/mesh of canaliculi produced by the expansion of the expanding material.

In a further embodiment, the biomaterial in fluid form should be prepared by the clinician immediately before use on the patient.

In an example, such embodiment provides for a step of joining a solid component in powder form with a component liquid preserved separately and hermetically.

The component in powder form (for example 100 g) comprises: a component adapted to form a porous structural matrix, for example an acrylic polymer, at a concentration of 100% w/w and a soluble component in powder and granular form, for example beta TCP, at a concentration variable between 1-50% w/w.

Such component in powder form should be preserved with a moisture content variable between 1 and 50% w/w.

The liquid component (for example 50 g) comprises an acrylic monomer such as methylmethacrylate, at a concentration of 97-99% w/w and an accelerator such as N—N dimethyl-p-toluidine, at a concentration variable between 1-3% w/w.

The two components, in powder and liquid form, are intimately mixed and the resulting fluid paste should be applied during surgery. After a few minutes, the paste becomes solid. In this case, the soluble component is dissolved upon contact with the biological fluids with which it comes to contact during surgery.

The method according to the present invention further comprises a step of providing porosity obtained according to the steps of provision of a soluble component, positioning the biomaterial at contact with biological liquids and/or water, dissolution and/or solubilisation of the soluble component, elimination of the dissolved soluble component with ensuing provision of empty spaces which form microcavities and macrocavities.

The dissolution of the soluble component is determined by water or liquids of various types or by biological fluids.

The method, in a further version, comprises a step of adding radiopaque materials—for example barium sulphate and/or other known radiopaque materials—to the biomaterial according to the present invention.

The method, in a version of an embodiment, comprising a step of adding chemical active ingredients, possibly with drug function, to the biomaterial.

This addition step, in the step of an embodiment, comprises a step of introducing the active ingredients in solid powder form to be added to the component in powder form before mixing with the liquid component, for providing a biomaterial in fluid form.

In a further embodiment step, this addition step comprises a step of introducing said active ingredients in aqueous solution state to be mixed with the preformed biomaterial due to the porous nature and capacity thereof to absorb liquids through capillarity.

In an embodiment of the method for obtaining the biomaterial according to the present invention, there is comprised a step of extruding the biomaterial through extrusion means of the known type, such as for example a syringe, and subsequent solidifying of the biomaterial which assumes, in such a manner, the characteristics of a structural matrix with the desired support capacity.

In an alternative embodiment, the method according to the invention comprises a step of obtaining a preform through thermal solidification or thermal sintering of the biomaterial so as to obtain a compact biocompatible composite material having a preformed shape.

Such preformed shape can be a cube, a plate or any other shape useable for replacing the damaged bone tissue or for the introduction of the same into a bone lacuna.

Such method can further comprise a step of resizing the biomaterial of preformed shape through the common instruments used in orthopaedics.

Such steps can also be present at an order different from the one indicated above and they can be present, contingently, wholly or partly, with respect to the various embodiments described above.

The invention claimed is:

1. A composite biocompatible biomaterial, useable as a drug delivery system, a spacer or a bone substitute, comprising:
    a structural matrix component comprising polymethyl methacrylate, and a soluble component comprising tricalcium phosphate, wherein said tricalcium phosphate comprises both powder and granules, wherein the structural matrix component includes canaliculi having a dimension of smaller than 100 microns and partially housing the soluble component,
    and wherein the structural matrix component and the soluble component comprises a moisture content between 1 and 50% w/w,
    wherein said tricalcium phosphate powder has a dimension smaller than 100 microns, and wherein said tricalcium phosphate powder dissolves when contacted with a liquid to form empty spaces which constitute a porosity formed by microcavities with dimensions smaller than 100 microns, and
    wherein said tricalcium phosphate granules have dimensions between 200 and 500 microns and wherein said tricalcium phosphate granules dissolve when contacted with a liquid to form empty spaces which constitute a porosity formed by macrocavities with dimensions between 200 and 500 microns, to impart mechanical support characteristics and osteoinductive and osteoconductive characteristics in the entire volume occupied by said biomaterial.

2. The biomaterial according to claim 1, wherein said structural matrix component further comprises one or more components selected from the group comprising: polymeric components, pure metal components, alloys and ceramic components.

3. The biomaterial according to claim 1, wherein said soluble component further comprises at least one of a calcium bioceramic inorganic material, inorganic salts provided with solubility and biocompatibility, or soluble organic substances.

4. The biomaterial according to claim 1, wherein said macrocavities are spherical-shaped.

5. The biomaterial according to claim 1, wherein said biomaterial further comprises radiopaque materials, comprising barium sulphate and/or other radiopaque materials.

6. The biomaterial according to claim 1, wherein said structural matrix component is in fluid or solid form.

7. The biomaterial according to claim 6, wherein said biomaterial comprising said structural matrix component in fluid form is injectable.

8. The biomaterial according to claim 6, wherein said biomaterial comprising said structural matrix component in solid form has a preformed shape.

9. A method for obtaining a biocompatible composite material, usable as a drug delivery system, a spacer or bone substitute, comprising the following steps:
    providing a structural matrix component comprising polymethyl methacrylate;
    providing a soluble component comprising both tricalcium phosphate powder and granules;
    wherein said step of providing said soluble component comprises
    providing tricalcium phosphate powder with a dimension smaller than 100 microns and providing tricalcium phosphate granules with dimensions between 200 and 500 microns;
    mixing said polymethyl methacrylate and said tricalcium phosphate;
    dissolving said tricalcium phosphate to form empty spaces which constitute a porosity formed by microcavities with a dimension smaller than 100 microns and
    empty spaces which constitute a porosity formed by macrocavities with dimensions between 200 and 500 microns, so as to have mechanical support characteristics and osteoinductive and osteoconductive characteristics in the entire volume occupied by said biomaterial;
    wherein the structural matrix component includes canaliculi having a dimension of smaller than 100 microns and partially housing the soluble component, and wherein the structural matrix component and the soluble component comprises a moisture content between 1 and 50% w/w.

10. The method according to claim 9, wherein said step of providing said structural matrix component further comprises providing one or more components selected from the group comprising: polymeric components, pure metal components, alloys, and ceramic components.

11. The method according to claim 9, wherein said soluble component in the form of powder and granules further at least one of a calcium bioceramic inorganic material, inorganic salts with solubility and biocompatibility, or soluble organic substances.

12. The method according to claim 9, further comprising a step of
thermal polymerisation or solidification or thermal sintering of said biomaterial.

13. The method according to claim 9, further comprising a step of adding radiopaque materials to said biomaterial.

14. The method according to claim 9, further comprising a step of adding chemical active ingredients comprising drugs to said biomaterial.

15. The method according to claim 14, wherein said adding step comprises introducing said active ingredients in solid powder form.

16. The method according to claim 14, wherein said adding step comprises introducing said active ingredients in aqueous solution.

17. The biomaterial of claim 3, further comprising polysaccharides comprising lactose, and carbohydrates comprising amides.

18. The method of claim 11, further comprising polysaccharides comprising lactose, and carbohydrates comprising amides.

19. A composite biocompatible biomaterial, useable as a drug delivery system, a spacer or a bone substitute, comprising:

a structural matrix component consisting of polymethyl methacrylate;
a soluble component consisting of tricalcium phosphate, wherein the structural matrix component includes canaliculi having a dimension of smaller than 100 microns and partially housing the soluble component,
and wherein the structural matrix component and the soluble component comprises a moisture content between 1 and 50% w/w; and
a radiopaque material;
wherein said tricalcium phosphate comprises both powder and granules, wherein said tricalcium phosphate powder has a dimension smaller than 100 microns, and wherein said tricalcium phosphate powder dissolves when contacted with a liquid to form empty spaces which constitute a porosity formed by microcavities with dimensions smaller than 100 microns, and wherein said tricalcium phosphate granules have dimensions between 200 and 500 microns and wherein said tricalcium phosphate granules dissolve when contacted with a liquid to form empty spaces which constitute a porosity formed by macrocavities with dimensions between 200 and 500 microns, to impart mechanical support characteristics and osteoinductive and osteoconductive characteristics in the entire volume occupied by said biomaterial.

20. The composite biocompatible biomaterial of claim 19, further comprising at least one chemically active ingredient.

* * * * *